United States Patent [19]

Mussmann

[11] Patent Number: 4,557,902
[45] Date of Patent: Dec. 10, 1985

[54] TESTING TUBE AND TESTING TUBE FILTER ASSEMBLY THEREFOR

[75] Inventor: Bernd Mussmann, Lübeck, Fed. Rep. of Germany

[73] Assignee: Drägerwerk A.G., Fed. Rep. of Germany

[21] Appl. No.: 376,186

[22] Filed: May 7, 1982

[30] Foreign Application Priority Data

May 13, 1981 [DE] Fed. Rep. of Germany ....... 3118878

[51] Int. Cl.$^4$ .................... B01D 46/10; G01N 21/78
[52] U.S. Cl. .................................. 422/59; 55/493; 210/451; 210/455; 422/101
[58] Field of Search ............... 422/59, 60, 86, 88, 422/101; 210/451, 455, 477; 55/493, 501, 503

[56] References Cited

U.S. PATENT DOCUMENTS

| | | | |
|---|---|---|---|
| 3,295,686 | 1/1967 | Krueger | 210/455 |
| 3,463,322 | 8/1969 | Gerarde | 210/455 |
| 4,123,228 | 10/1978 | Frei et al. | 210/477 X |
| 4,272,479 | 6/1981 | Huneke et al. | 422/60 X |
| 4,330,297 | 5/1982 | Leichnitz | 422/86 X |

*Primary Examiner*—Arnold Turk
*Attorney, Agent, or Firm*—McGlew and Tuttle

[57] ABSTRACT

A testing tube comprises a glass tube having breakable tips at each end which may be broken to facilitate the passage of gas to be tested through the tube. The tube is separated by a plurality of mounting elements for resilient discs into a plurality of separate chambers which includes a chamber having a breakable ampule therein and a chamber having a layer of reaction material therein. In addition, the test tube contains a filter element which is located between two adjacent chambers. The filter element comprises a tubular ring member which is insertable in the glass tube and has an outwardly flaring end adjacent one end which bears tightly against the walls of the tube and permits the insertion of a filter disc into the flaring end so that it rests against a support ledge in the bore of the ring member. The filter is held by a cover portion which includes a resilient ring having a bead which engages into a groove defined in the bore overlying the ledge.

7 Claims, 3 Drawing Figures

1

TESTING TUBE AND TESTING TUBE FILTER ASSEMBLY THEREFOR

FIELD AND BACKGROUND OF THE INVENTION

This invention relates in general to the construction of testing tubes and in particular to a new and useful filter element for such tubes.

Testing tubes are generally known. They are used in combination with manual or automatic pumps for the qualitative or quantitative analysis of gases, vapors or aerosols. Before the gas-tight test tubes are used, their tips are broken off, and a certain volume of the medium to be tested is sucked through. The testing tube contains certain reagents, which then form with the respective medium mostly colored reaction products. The applicant's assignee supplies about 200 different test tubes for the various media. A major part of the test tubes is equipped with a filter part to be traversed by the test medium.

A known testing tube for measuring arsenic trioxide aerosols in air contains in the glass tubes provided with break-off tips successively in the direction of flow, a reagent ampule filled with diluted sulfuric acid, a filter paper flush with the glass wall and impregnated with zinc powder, a granular collecting layer of silica gel, a granular separating layer of inert quartz, and a granular indicating layer of silica gel impregnated with gold chloride. The filter is held by an elastic holding element on the silica gel layer. Above the holding element is then the reagent ampule, which is held at its other end again by a holding element. A complete deposit of the aerosols on the filter paper, which is necessary for an exact evaluation, requires a tight seal on the inner wall of the glass tube. This is very difficult to achieve, due to the great manufacture-related tolerances of the glass tubes and of the other elements (German Pat. No. 2,926,711).

SUMMARY OF THE INVENTION

The invention provides a filter element which is simple to manufacture, can be easily inserted into the test tube, and seals tightly on the inner wall of the glass tube.

In accordance with the invention, there is provided a testing tube construction which comprises a glass tube which has breakable tips at each end which may be broken to facilitate the passage of a gas to be tested therethrough. There are a plurality of separate chambers defined in the test tube by spacing elements or mounts and including one chamber that has a breakable ampule and another chamber that has a layer of a reaction material which reacts with the liquid of the ampule to give a testing result for the gas which is passed therethrough. The construction also includes a filter element which in accordance with the invention is contained in a resilient mounting in the form of a ring or tube having a through bore therethrough with a ledge in the bore against which a filter disc is positioned which includes a cover element having a bead which engages with a groove of the bore defined above the ledge so as to tightly hold the filter element in position and providing a passage through the ring cover and the ring support member for the filter for the gas to be tested.

The essential advantage lies in the simple handling, which ensures a tight bearing of the filter discs which can then really perform their functions. Despite all the mechanization, it was not simple heretofore to insert a round filter disc of 4 to 5 mm, which is sensitive to handle, up to 100 mm into a glass tube with an inside diameter of 4 to 5 mm bearing tightly on the inner wall.

The embodiment according to this solution produces a filter element provided with tight holding elements, which are completely finished before the assembly. The parts used permit automatic mechanical production and they only have to be pushed into the tubes down to the desired department. This is enhanced by the frustrum-shaped holding shoulder. The filter elements are simple and safe to use in all test tubes in which filter discs are required, hence both in gas-vapor-and aerosol test tubes. The design also permits the use as a mount for other parts of the test tube.

Accordingly, it is an object of the invention to provide an improved testing tube construction and to an improved filter and filter holder construction therefor which includes a filter element located between chambers of the testing tube including a resilient ring member having a ledge thereon which carries a filter disc and with an annular groove defined in the member overlying the ledge which receives a beaded rim of a cover engaged over the filter disc.

A further object of the invention is to provide a testing tube construction and a filter disc therefor, which are simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
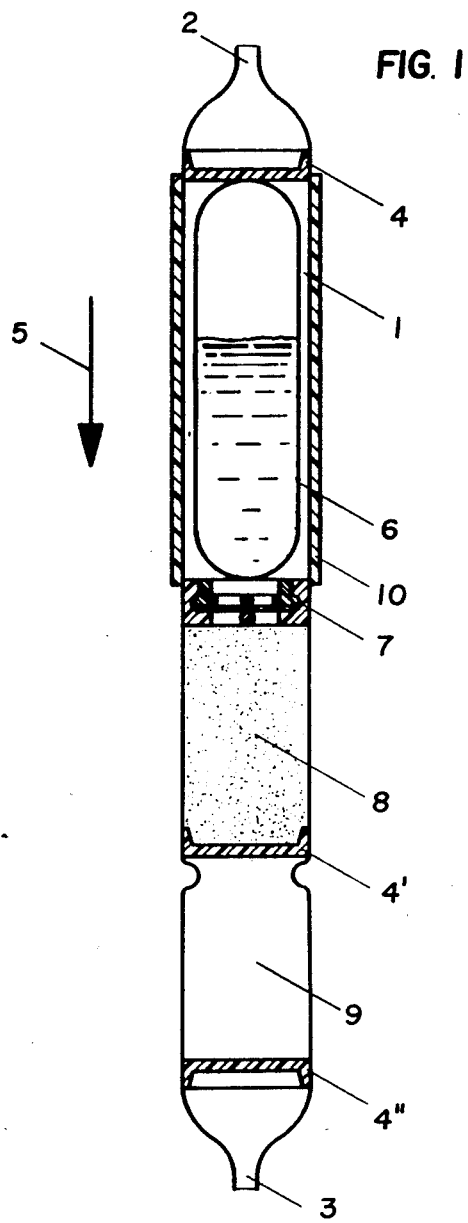
FIG. 1 is a sectional view of a testing tube constructed in accordance with the invention.
Figure 2:
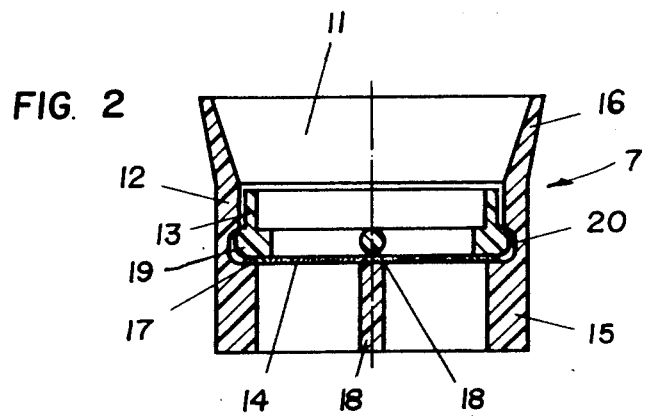
FIG. 2 is an enlarged sectional view of the filter element used in the testing tube of FIG. 1.

Referring to the drawings, in particular the invention embodied therein in FIGS. 1 and 2, comprises a testing tube construction which includes a glass tube 1 having breakable tips at each end 2 and 3 which may be broken to facilitate the passage of a gas to be tested therethrough. Means such as mounts or resilient disc separators 4,4',4" etc. are provided to separate the interior of the testing tube into a plurality of separate chambers which includes a chamber containing an ampule 6 which is breakable after a gas is circulated through the tube to cause a reaction liquid to flow through the characteristic elements picked up by a filter 7 to produce a reaction in a reaction layer of material 8 arranged in a separate chamber. In accordance with the invention, the filter element 7 is arranged between two adjacent chambers and it comprises a tubular ring member 11 which is insertable in the glass tube and has an outwardly flaring end 16 adjacent one end which is tightly engageable with the wall of the tube. The tubular ring member 11 has a through bore therethrough and a lower cylindrical portion 15 in which is defined a filter support ledge 17 in a groove 20 overlying the ledge such as is shown in FIG. 2. A filter disc 14 is positioned on the ledge 17 and a cover ring 13 is arranged so as to overly the filter disc and it includes a ring bead 19 whch engages into a groove 20 defined over the ledge 17.

FIG. 1 shows a $H_2SO_4$ aerosol test tube or testing tube with filter element 7 according to the invention. The construction includes a tube 1 of glass with two break-off tips 2 and 3. The fillings are held shake proof between resilient tubes or mounts 4,4′ and 4″ in its various sections. The contents includes, in the direction of flow 5, a breakable reagent ampule 6 filled with reagent solution, a self holding filter element 7 and a reaction layer 8. This is followed by a chamber 9, closed by a moisture repellant mount 4″ for the discolored reaction solution. At the level of reagent ampule 6, tube 1 of glass is scored and covered with a shrunk on hose 10. This permits both the breaking of glass tube 1, and then the breaking of reagent ampule 6.

Filter element 7 is shown in FIG. 2. It includes an elastic mount 11 of a holding part, generally designated 12 with a cover 13, which receives between them filter disc 14 tightly bearing on a shoulder 17.

Holding part 12 comprises a cylindrical ring which continues into an outwardly and upwardly flaring frustum-shaped jacket portion 16 for holding on the inner wall of the tube 1. Filter disc 14 is supported by the circumferential shoulder 17. The free hole cross section is bridged over by radial supporting straps or ribs 18. Cover 13 with the same hole image has a circumferential bead 19, with which it engages a corresponding groove 20 when inserted into the holding part, and thus completes filter element 7 with the tightly bearing filter disc 14.

Filter element 7 can be used as a compact, easy to handle part in all types of test tubes at any desired point.

Figure 3:
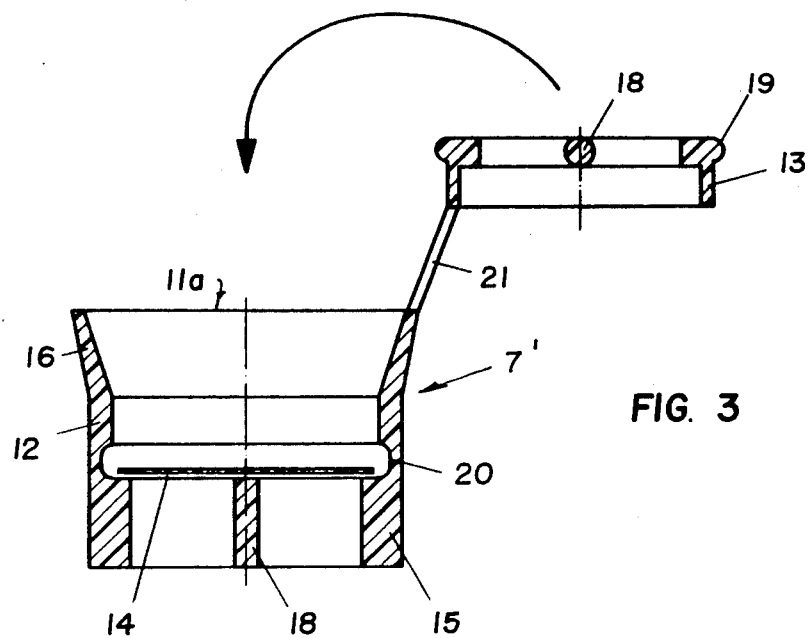
FIG. 3 is a view similar to FIG. 2 of another embodiment of the invention.

FIG. 3 shows mount 11a of another embodiment 7′ which includes a directly fastened cover portion 13′. It is integral with holding part 12 by means of a band or web 21. For buttoning-in cover 13′, band 21 bends accordingly.

While specific embodiments of the invention have been shown and described in detail to illustrate the application of the principles of the invention, it will be understood that the invention may be embodied otherwise without departing from such principles.

What is claimed is:

1. A testing tube construction, comprising a glass tube having breakable tips at each end which may be broken to facilitate the passage of a gas to be tested therethrough, means defining a plurality of separate chambers in said glass tube including a chamber having a breakable ampule therein and a chamber having a layer of reaction material therein, and a filter element in said tube between two adjacent chambers comprising a tubular ring member insertable in said glass tube having an outwardly flaring end adjacent one end which is tightly engageable with the wall of said glass tube and having a through bore therethrough with a filter support ledge in said bore and a groove in said bore overlying said support ledge, a filter disc insertable through the outwardly flaring end and engageable on said ledge, and cover means having a gas passage therethrough overlying said filter disc and having a rim bead engaged in said groove, said cover means being adapted to hold said filter disc in position on said ledge.

2. A testing tube according to claim 1, wherein said tubular ring member includes a radially extending support strap extending across said bore over which said filter disc is positioned.

3. A testing tube according to claim 1, wherein said cover means is formed integrally with said tubular ring member and includes a web portion which interconnects with said tubular ring member.

4. A testing tube according to claim 1, wherein said tubular ring member comprises an extrudable plastic material.

5. A filter element for use in a testing tube comprising a tubular ring member insertable in the testing tube having an outwardly flaring end adjacent one end which is tightly engageable with the walls of said tube, said ring member having a through bore therethrough with a filter support ledge defined in said bore and a groove defined in said bore overlying the ledge, a filter disc insertable through the outwardly flaring end and engageable on said ledge, and cover means overlying said filter disc and having a rim bead engaged in said groove, said cover means being adapted to hold said filter disc in position in said ring member and including means for gas passage.

6. A filter element according to claim 5, wherein said cover ring includes a diametrical rib, said tubular ring member having a diametrical rib engageable with said filter disc below the diametrical rib of said cover.

7. A filter element according to claim 5, wherein said outwardly flaring end includes a web extension formed integrally with said cover.

* * * * *

UNITED STATES PATENT AND TRADEMARK OFFICE
CERTIFICATE OF CORRECTION

PATENT NO.  : 4,557,902

DATED       : December 10, 1985

INVENTOR(S) : Bernd Mussmann

It is certified that error appears in the above-identified patent and that said Letters Patent is hereby corrected as shown below:

The term of this patent subsequent to June 10, 2000, has been disclaimed.

Signed and Sealed this

Twenty-sixth Day of January, 1988

Attest:

DONALD J. QUIGG

Attesting Officer

Commissioner of Patents and Trademarks